United States Patent
Zhang et al.

(10) Patent No.: US 10,531,817 B2
(45) Date of Patent: Jan. 14, 2020

(54) FALL DETECTION METHOD AND SYSTEM

(71) Applicant: Peking University, Beijing (CN)

(72) Inventors: Daqing Zhang, Beijing (CN); Hao Wang, Beijing (CN); Yasha Wang, Beijing (CN)

(73) Assignee: Peking University, Beijing (CN)

( * ) Notice: Subject to any disclaimer, the term of this patent is extended or adjusted under 35 U.S.C. 154(b) by 0 days.

(21) Appl. No.: 16/071,336

(22) PCT Filed: Nov. 4, 2016

(86) PCT No.: PCT/CN2016/104748
§ 371 (c)(1),
(2) Date: Jul. 19, 2018

(87) PCT Pub. No.: WO2017/124816
PCT Pub. Date: Jul. 27, 2017

(65) Prior Publication Data
US 2019/0175074 A1  Jun. 13, 2019

(30) Foreign Application Priority Data

Jan. 20, 2016 (CN) .......................... 2016 1 0036013

(51) Int. Cl.
*A61B 5/11* (2006.01)
*H04B 17/336* (2015.01)
(Continued)

(52) U.S. Cl.
CPC .......... *A61B 5/1117* (2013.01); *G08B 21/043* (2013.01); *H04B 7/0413* (2013.01); *H04B 7/22* (2013.01); *H04B 17/336* (2015.01)

(58) Field of Classification Search
CPC .................... A61B 5/1117; H04B 17/336; H04B 17/0413; H04B 17/22; G08B 21/043
(Continued)

(56) References Cited

U.S. PATENT DOCUMENTS

| 6,720,874 B2* | 4/2004 | Fufido ................ G07C 9/00031 |
| | | 340/5.2 |
| 2010/0245091 A1* | 9/2010 | Singh ..................... A61B 5/024 |
| | | 340/573.1 |

(Continued)

FOREIGN PATENT DOCUMENTS

| CN | 103606248 | * | 2/2014 |
| CN | 103606248 A | | 2/2014 |

(Continued)

OTHER PUBLICATIONS

Scholkpf, B. et al., "Estimating the Support of a High-Dimensional Distribution," Neural Computation, vol. 13, No. 7, Jul. 2001, 29 pages.

(Continued)

*Primary Examiner* — Omar Casillashernandez
(74) *Attorney, Agent, or Firm* — McCoy Russell LLP

(57) ABSTRACT

The present invention relates to a fall detection method and system. The fall detection method comprises: receiving, by a first receiving antenna, a first WiFi signal stream propagating through an environment; receiving, by a second receiving antenna, a second WiFi signal stream propagating through the environment; determining a physical layer Channel State Information (CSI) stream, namely, a first CSI stream, of the first WiFi signal stream; determining a physical layer CSI stream, namely, a second CSI stream, of the second WiFi signal; determining a phase difference, namely, a CSI phase difference, between respective phase of the physical layer CSI stream of the first WiFi signal stream and the physical layer CSI stream of the second WiFi signal stream at the same time point, to form a CSI phase difference stream; and determining, according to the CSI streams and the CSI phase difference stream, a fall event.

7 Claims, 9 Drawing Sheets

(51) Int. Cl.
*G08B 21/04* (2006.01)
*H04B 7/0413* (2017.01)
*H04B 7/22* (2006.01)

(58) Field of Classification Search
USPC .................................................... 340/573.1
See application file for complete search history.

(56) References Cited

U.S. PATENT DOCUMENTS

| | | | | |
|---|---|---|---|---|
| 2012/0146796 | A1* | 6/2012 | Margon | A61B 5/05 340/573.1 |
| 2013/0002434 | A1* | 1/2013 | Cuddihy | G08B 21/043 340/573.7 |
| 2014/0155729 | A1* | 6/2014 | Saitoh | G01S 13/40 600/407 |
| 2015/0206409 | A1* | 7/2015 | Visvanathan | A61B 5/002 340/573.1 |
| 2015/0276963 | A1* | 10/2015 | Casimiro | G08B 13/26 324/658 |
| 2016/0077123 | A1* | 3/2016 | Kagaya | A61B 5/1113 702/150 |
| 2016/0203692 | A1* | 7/2016 | Ten Kate | G08B 21/043 340/573.1 |
| 2018/0003847 | A1* | 1/2018 | Casimiro | A61B 5/1117 |
| 2018/0292523 | A1* | 10/2018 | Orenstein | G08B 21/043 |

FOREIGN PATENT DOCUMENTS

| | | |
|---|---|---|
| CN | 104586402 A | 5/2015 |
| CN | 104951757 A | 9/2015 |
| CN | 105933080 A | 9/2016 |
| WO | 2013056731 A1 | 4/2013 |

OTHER PUBLICATIONS

IEEE Standards Association, IEEE Standard for Information technology—Telecommunications and information exchange between systems—Local and metropolitan area networks—Specific requirements, IEEE Std 802.11n-2009, Oct. 29, 2009, 536 pages.

Han, C. et al., "WiFall: Device-free Fall Detection by Wireless Networks," Proceedings of the IEEE INFOCOM 2014—IEEE Conference on Computer Communications, Apr. 27, 2014, Toronto, Ontario, Canada, 9 pages.

Nandakumar, R. et al., "WiFi Gesture Recognition on Existing Devices," University of Washington, Department of Computer Science and Engineering, Nov. 2014, 5 pages.

ISA State Intellectual Property Office of the People's Republic of China, International Search Report Issued in Application PCT/CN2016/104748, dated Jan. 26, 2017, WIPO, 4 pages.

* cited by examiner

FALL DETECTION METHOD AND SYSTEM

CROSS-REFERENCE TO RELATED APPLICATIONS

The present application is a U.S. National Phase of International Patent Application Serial No. PCT/CN2016/104748, entitled "FALL DETECTION METHOD AND SYSTEM," filed on Nov. 4, 2016. International Patent Application Serial No. PCT/CN2016/104748 claims priority to Chinese Patent Application No. 201610036013.3, filed on Jan. 20, 2016. The entire contents of each of the above-cited applications are hereby incorporated by reference in their entirety for all purposes.

TECHNICAL FIELD

The present invention relates to the field of fall detection, and in particular, to a real-time and contactless fall detection method and system with commodity WiFi devices.

BACKGROUND

Falls are the leading cause of fatal and nonfatal injuries to elders in the modern society. For elders who live alone and independently, about 50% of the falls occur within their own homes, thus timely and automatic detection of falls has long been the research goal in the assistive living community. Various techniques ranging from wearable sensor-based, ambient device-based to computer vision based solutions have been proposed and studied. Wearable sensor-based approaches were among the first techniques developed for fall detection. Since Lord and Colvin proposed an accelerometer-based approach in 1991, numerous kinds of sensors have been explored for fall detection in the past few decades, ranging from gyroscopes, barometric pressure sensors, RFID, to the sensor-rich smart phones. These systems can only work when sensors are worn by the user. However, the always-on-body requirement makes the subject difficult to comply with, especially for the elders at home. Ambient device-based approaches try to make use of ambient information caused by falls to detect the risky activity. The ambient information being used includes audio noise, floor vibration, and infrared sensing data. In these systems, dedicated devices need to be implanted in the environment. However, the other sources of pressure or sound around the subject in the environment account for a large proportion of false alarms. Computer vision-based approaches use cameras installed in the monitoring environment to either capture images or video sequences for scene recognition. Although the recent advances in infra-red LED and depth camera like Microsoft Kinect, have enlarged its application scope (e.g., independent of illumination of lights and can work even in a dark room), the privacy intrusions, inherent requirement for line of sight and intensive computation for real-time processing are still open issues that need to be addressed in the future.

Due to the limitations of the above-mentioned fall detection solutions, very few fall detection systems have been widely deployed in real home settings so far. In recent years, the rapid development in wireless techniques has stimulated the research in studying the relationship between the wireless signal and human activities. In particular, the recently exposed physical layer Channel State Information (CSI) on commercial WiFi devices reveals multipath channel features at the granularity of OFDM subcarriers, which is much finer-grained than the traditional MAC layer RSS (Received Signal Strength). By exploiting the amplitude and phase information of CSI across the OFDM subcarrier and the diversity of CSI information across multi-antennas in the MIMO system, significant progress has been made in applications in motion detection, lip language and gesture recognition, vital sign monitoring and activity recognition. The rationale behind all these research efforts is that different human activities can cause different signal change patterns, and activities can be recognized in real-time by mapping the observed signal change patterns to different human activities.

In the prior art, there is a technology using WiFi commodity devices to detect fall. However, it makes two assumptions: (1) the subject can only perform four kinds of predefined activities (i.e., walk, sit, stand up, fall); (2) Activities can not be performed continuously. For example, the subject should stand up and stand for a while, and then walk. Wifall proposed by C. Han, K. Wu, Y. Wang and L. M. Ni in "Wifall: Device-free fall detection by wireless networks" is an example. Both assumptions are not realistic in real home settings. Therefore, in the present invention, the inventors intend to remove both assumptions to detect the fall in the real settings, i.e., various daily activities are performed naturally and continuously.

In order to automatically detect falls in real-time with WiFi signals in the real settings, there are several challenges that must be addressed. Firstly, how the fall and other human activities affect the amplitude and phase information of CSI? Are there any specific features in the CSI of WiFi signal streams which can characterize the fall and other human activities? Secondly, as activities are performed continuously, the boundary of the WiFi signal of subsequent activities is not given. How to automatically and accurately segment the corresponding fall and other activities in the continuously captured WiFi wireless signal streams? Thirdly, as there are countless daily activities, from the perspective of activities recognition, the problem space is infinite. Even if the activities are segmented out, differentiating the fall from all the other daily activities is like searching a solution in an infinite problem space, which is also challenging.

The inventors observe that the phase difference over two antennas exhibits interesting characteristics in the presence of fall and other human activities. Based on this observation, the inventors proposed a transition-based segmentation method leveraging the variance of phase difference over a pair of receiver antennas as a salient feature to automatically segment all the fall and fall-like activities in the continuously captured WiFi wireless signal streams. Then the inventors extracted features from both the amplitude and phase information of CSI to separate the fall from the fall-like activities. In addition to verifying that the phase difference is a more sensitive base signal than the amplitude of CSI, the inventors also observed that the fall and fall-like activities are ended with a sharp power profile decline in the time-frequency domain. Based on these two insights, the inventors design and implement inventors' real-time fall detector, called RT-Fall.

The main contributions of the present invention are as follows:

1) Deal with fall detection problem with commodity WiFi devices in the real settings, i.e., detect the fall in the condition that countless daily activities are performed naturally and continuously.

2) Identify the phase difference of CSI as a better base signal than amplitude for activity segmentation and fall detection. By studying the relationship between different human activities and the variance of phase difference, the inventors demonstrate its effectiveness as a base signal to segment the fall and fall-like activities in the continuously captured signal streams.

3) The inventors found the sharp power profile decline pattern of the fall in the time-frequency domain and further exploited the complementary characteristics of falls in the time and frequency domain for accurate fall segmentation/detection.

4) The inventors design and implement the real-time activity segmentation and fall detection system, RT-Fall on commodity WiFi devices, with only one antenna at the transmitter side, and two antennas at the receiver side. Experimental results demonstrate that RT-Fall can accurately segment fall and fall-like activities in WiFi wireless signal streams, and has a better fall detection performance than WiFall, the highest level fall detector currently available.

SUMMARY

According to one aspect of the present invention, a fall detection method is provided. This fall detection method may be performed by using a receiver having at least two WiFi receiving antennas, such as by using a notebook computer with at least two WiFi receiving antennas.

According to one embodiment of the present invention, in the fall detection method, WiFi signal streams can be transmitted to the environment via a transmitting antenna of a WiFi transmitting device at S110. Wherein, the WiFi transmitting device may use orthogonal frequency division modulation (OFDM) in the physical layer.

This fall detection method, comprises: receiving a first WiFi signal stream propagating through an environment by a first receiving antenna at S120; receiving a second WiFi signal stream passing through the environment by a second receiving antenna at S130; determining a physical layer Channel State Information stream, namely, a first CSI stream, of the first WiFi signal stream at S140; determining a physical layer Channel State Information stream, namely, a second CSI stream, of the second WiFi signal stream at S150; determining a phase difference between the physical layer Channel State Information stream of the first WiFi signal stream and the physical layer Channel State Information stream of the second WiFi signal stream at the same time point, namely, a CSI phase difference, to form a physical layer Channel State Information phase difference stream, namely, CSI phase difference stream at S160; and determining a fall event according to the phase difference stream between the physical layer Channel State Information stream of the first WiFi signal stream and the physical layer Channel State Information stream of the second WiFi signal stream, namely, the CSI phase difference stream at S170. In a further embodiment, determine a fall event according to the first and second CSI streams. Wherein, at the same time point, the first receiving antenna receives the first CSI of wireless signal having respective a first amplitude and a first phase, which reflects the influence of the environment before the wireless signal reaches the first receiving antenna on the signal; at this same time point, the second receiving antenna receives the second CSI of wireless signal having respective a second amplitude and a second phase, which reflects the influence of the environment before the wireless signal reaches the second receiving antenna on the signal. The CSI phase difference at the same time point refers to a phase difference between the first phase of the first CSI at this time point and the second phase of the second CSI at this time point.

Those skilled in the art can understand that two independent sets of antennas can also be used, such as two sets of receiving devices respectively configured with two receiving antennas for receiving the WiFi signal streams transmitted by the transmitting antenna of the WiFi transmitting device. A plurality of receiving antennas can also be used, such as three or more receiving antennas to receive the WiFi signal stream transmitted by the transmitting antenna of the WiFi transmitting device. Then, the method of the present invention is applied for the physical layer Channel State Information stream of WiFi signal streams received by a plurality of antennas, namely, the phase difference between a plurality of CSI streams.

According to one embodiment of the present invention, in the fall detection method, the first WiFi signal stream is the WiFi signal stream transmitted by the WiFi transmitting device and received by the first receiving antenna, the second WiFi signal stream is the WiFi signal stream transmitted by the WiFi transmitting device and received by the second receiving antenna.

According to one embodiment of the present invention, in the fall detection method, the finishing reference point for fall or fall-like activities may be identified based on the CSI phase difference and a starting reference point for fall or fall-like activities may be determined based on the trace back window size.

According to one embodiment of the present invention, in the fall detection method, interpolation may be performed among the CSI streams in order to get an interpolated CSI streams with a continuous time-frequency domain spectrum; removing the uncorrelated signal frequency components from the interpolated CSI streams to get a band-pass filtered CSI phase difference streams; wherein a finishing reference point for fall or fall-like activities is identified based on the band-pass filtered CSI phase difference and a starting reference point for fall or fall-like activities is determined based on the trace back window size.

According to one embodiment of the present invention, wherein, removing the uncorrelated signal frequency components according to the predetermined threshold.

According to one embodiment of the present invention, wherein, uncorrelated signal frequency components can be determined to be below 4 Hz or above 10 Hz. In this way, the uncorrelated signal frequency components may be removed from the interpolated CSI streams, for example, remove low-frequency components, or remove low-frequency components and high-frequency components, in order to retain the most significant intermediate frequency components.

According to one embodiment of the present invention, in the fall detection method, determining if a raw CSI phase difference signal and a band-pass filtered CSI phase difference signal are in a fluctuation state or a stable state by using a threshold-based sliding window method; and for the raw CSI phase difference signal and the band-pass filtered CSI phase difference signal, detecting the transition from the fluctuation state to the stable state, and determining a finishing reference point of fall and fall-like activities by checking if the two signals enter the stable state.

According to one embodiment of the present invention, in the fall detection method, wherein further comprising: wherein if and only if the raw CSI phase difference signal and the filtered CSI phase difference signal enter the stable state with a time difference according to the respective sliding standard deviation and the corresponding predetermined threshold, namely, the time lag, which is less than the predetermined threshold, determining a finishing reference point of fall and fall-like activities. Wherein, in one embodiment, the predetermined threshold is 2 seconds.

According to one embodiment of the present invention, in the fall detection method, wherein further comprising: extracting the following features of the raw CSI phase difference stream and/or the filtered CSI phase difference stream: power decline ratio (PDR) (taking the determined finishing reference point of a fall and fall-like activities as a base time point, the power decline ratio (PDR) is determined to be the energy decline ratio within a predetermined frequency range (for example, 0-50 Hz) within a predetermined time length before and after the base time point (for example, within two time windows of one second before and after) over the time-frequency spectrum); and determining a fall event according to the raw CSI phase difference streams and/or the filtered CSI phase difference streams.

According to one embodiment of the present invention, in the fall detection method, determining a fall event by using one-class Support Vector Machine (SVM) according to the time lag and the power decline ratio of the raw CSI phase difference stream or filtered CSI phase difference stream.

According to one embodiment of the present invention, in the fall detection method, wherein further comprising: extracting the following features of the first CSI stream or the second CSI stream (1) the normalized standard deviation (STD); (2) the median absolute deviation (MAD); (3) the offset of signal strength; (4) interquartile range (IR); (5) signal entropy; (6) the velocity of signal change; extracting the following features of the CSI phase difference (1) the normalized standard deviation (STD); (2) the median absolute deviation (MAD); (3) the offset of signal strength; (4) interquartile range (IR); (5) signal entropy; (6) the velocity of signal change; (7) time lag; (8) power decline ratio (PDR); and determining a fall event according to the features extracted by the feature extraction device by using one-class Support Vector Machine (SVM).

According to one embodiment of the present invention, in the fall detection method, wherein further comprising labeling the identified fall or fall-like activities, and providing the label and the respective extracted features to the one-class Support Vector Machine (SVM).

According to one embodiment of the present invention, a fall detection system is provided, this system includes WiFi receiving device, Channel State Information (CSI) processing module, and fall event determining module. The WiFi receiving device comprises a first receiving antenna and a second receiving antenna, wherein a first WiFi signal stream propagating through an environment is received by the first receiving antenna, and a second WiFi signal stream propagating through the environment is received by the second receiving antenna; Channel State Information (CSI) processing module, the Channel State Information (CSI) processing module configured to determine a physical layer Channel State Information (CSI) stream, namely, a first CSI stream, of the first WiFi signal stream; determine a physical layer Channel State Information (CSI) stream, namely, a second CSI stream, of the second WiFi signal stream; and determine the phase difference, namely, CSI phase difference, between the respective phase of the physical layer Channel State Information (CSI) stream of the first WiFi signal stream and the physical layer Channel State Information (CSI) stream of the second WiFi signal stream at the same time point, to form a CSI phase difference stream; and fall event determining module, the fall event determining module configured to determine a fall event according to the CSI phase difference stream. In a further embodiment, the fall event determining module is configured to determine a fall event according to the first and second CSI streams and the CSI phase difference stream.

According to one embodiment of the present invention, this fall event determining module further comprises a WiFi transmitting device. According to another embodiment of the present invention, the Channel State Information (CSI) processing module of the fall detection system further comprising interpolation module, filter module and activity segmentation module.

Various features, functions, and advantages may be independently embodied in various embodiments of the present invention or combined in various embodiments with the following description and accompanying drawings to understand the details of the present invention.

DETAILED DESCRIPTION OF EXAMPLE EMBODIMENTS

Channel State Information in IEEE 802.11n/ac

Figure 1:
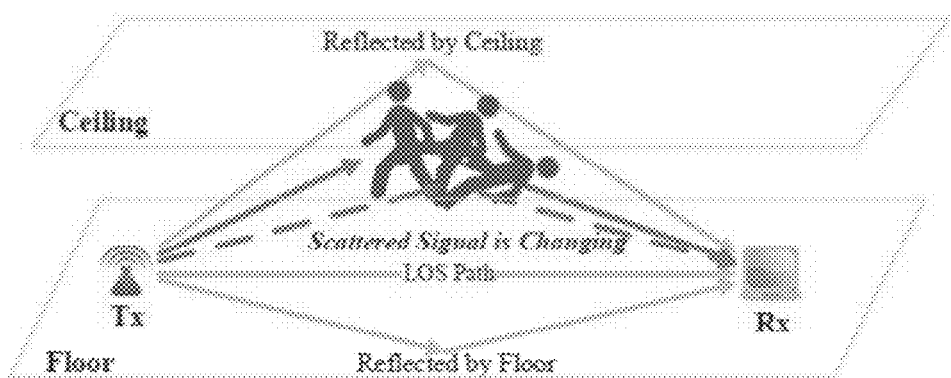
FIG. 1 shows WiFi signal propagation in indoor environment.

In a typical indoor environment, as illustrated in FIG. 1, WiFi signals propagate through the physical space via multiple paths such as ceiling, floor, wall and furniture. As the physical space constrains the propagation of wireless signals, the received signals in turn contain information that characterizes the environment they pass through. If a person presents in the environment, additional signal paths are introduced by the scattering (reflecting) of human body. So in the same way, the received signals also contain information that could characterize the existence (activity) of a person. If the inventors consider the physical space (including ambient subjects and human) as a wireless channel, the Channel State Information (CSI) depicts the effects when the wireless signals pass through this wireless channel. In frequency domain, the channel can be modeled as $$Y = HX + N$$

where Y and X are the received and the transmitted signal vectors respectively, N denotes the channel noise vector and H is the channel matrix. The channel matrix H is presented in the format of Channel State Information (CSI). Specifically, current WiFi standards (e.g., IEEE 802.11n/ac) use orthogonal frequency division modulation (OFDM) in their physical layer. OFDM splits its spectrum band (20 MHz) into multiple (56) frequency sub-bands, called subcarriers, and sends the digital bits through these subcarriers in parallel. CSI reveals a set of channel measurements depicting the amplitude and phase of every OFDM subcarrier. CSI of a single subcarrier is in the following mathematical format:

$$h = |h|e^{j\angle\theta},$$

where $|h|$ and $\theta$ are the amplitude and phase, respectively.

If there is no one or no motion in the environment, the wireless channel is relative stable. However, as shown in red lines in FIG. 1, along with the motion of a person, the scattered (reflected) signals are changing, which results in obvious channel distortion, involving both amplitude attenuation and phase shift. The rationale behind CSI behavior based recognition is that human activity can be recognized by mapping different channel distortion patterns caused by human activities to corresponding human activities.

Fall Activity Kinds Targeted

There are many ways in which an elder can fall, and in the present invention the inventors aim to detect falls occurred in situations with respect to two transition activities: 1): standing-fall refers to the situation that the fall occurs when an elder transfers out of a bed or chair, e.g., the elder may just stand up from the chair and feel dizzy due to cerebral ischemia; 2): walking-fall refers to situation that the fall occurs while an elder is walking.

Human Activities and Amplitude of CSI

As the inventors only use one transmitter antenna and two receiver antennas, CSI information the inventors collected is further divided into two wireless streams and thirty subcarriers in each stream. In this study, the inventors conduct experiments to see how the amplitude varies across different subcarriers and different streams respectively. The inventors have the same observation as that human activities affect different streams independently whereas affect different subcarriers in a similar way. Furthermore, subcarriers among adjacent frequencies share more similarities than those with larger frequency gap. Based on these observations, the inventors can average CSI samples of adjacent successive subcarriers into one signal value to achieve trade-off between computational complexity and functionality. In the rest of this description, the inventors will only show figures with one subcarrier in one stream.

Figure 2:
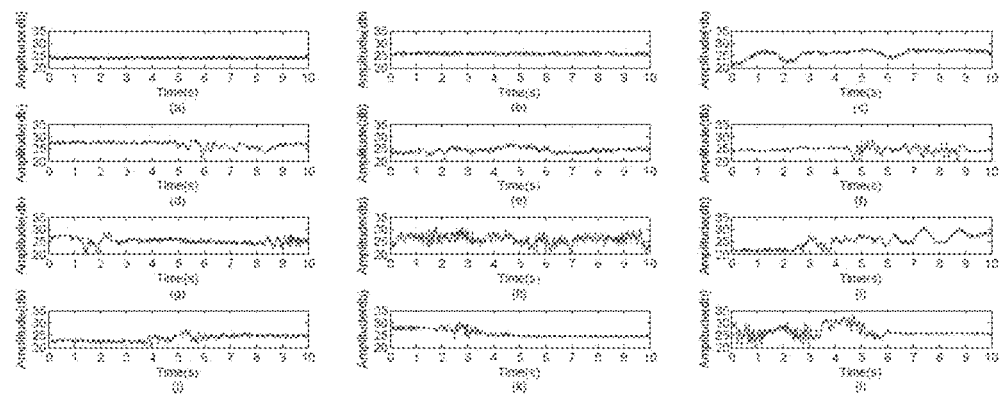
FIG. 2 shows CSI amplitude of human activities: (a) Sitting, (b) Lying, (c) Standing, (d) Lie down, (e) Upper body activities, (f) Pickup, (g) Squat, (h) Walking, (i) Stand up, (j) Sit down, (k) Standing-Fall, (l) Walking-Fall.

The inventors roughly divide human daily activities into two categories: immobile and motion activities. Impact of Immobile Human Activities, such as sitting and standing, intuitively result in relatively stable signal change patterns as they only involve tiny changes in human bodies (e.g., chest movement caused by respiration, tiny body movement unconsciously). Through extensive experiments, the results roughly fit the intuition. FIG. 2(a-c) shows the amplitude variance of three immobile activities, respectively. Interestingly, the inventors have an observation which was not mentioned in previous work: the signal variance of the standing posture is more notable than that of other immobile activities like sitting and lying. The inventors also note that the amplitude variance of standing reduces when the subject stands farther away from LOS path. Hence, the inventors doubts whether the amplitude can reliably distinguish between the standing posture and other immobile activities. This inspires the inventors to conduct a comprehensive analysis on the impact of LOS/NLOS condition before we can give the answer to this question. Impact of Human Motion Activities: Compared to immobile activities which result in relatively stable signal changes, motion activities, such as walking, lying down, sitting down and fall, exhibit obvious signal variance as illustrated in FIG. 2(d-l). To differentiate fall from other activities, the inventors tried to find some unique features of the fall at first. Unfortunately, neither the variance of the amplitude nor the profile of the amplitude shows clear patterns to make the fall distinguishable from other activities. Therefore, the amplitude can only tell whether the subject is conducting motion activities or not.

Activities in LOS and NLOS Conditions

Figure 3:
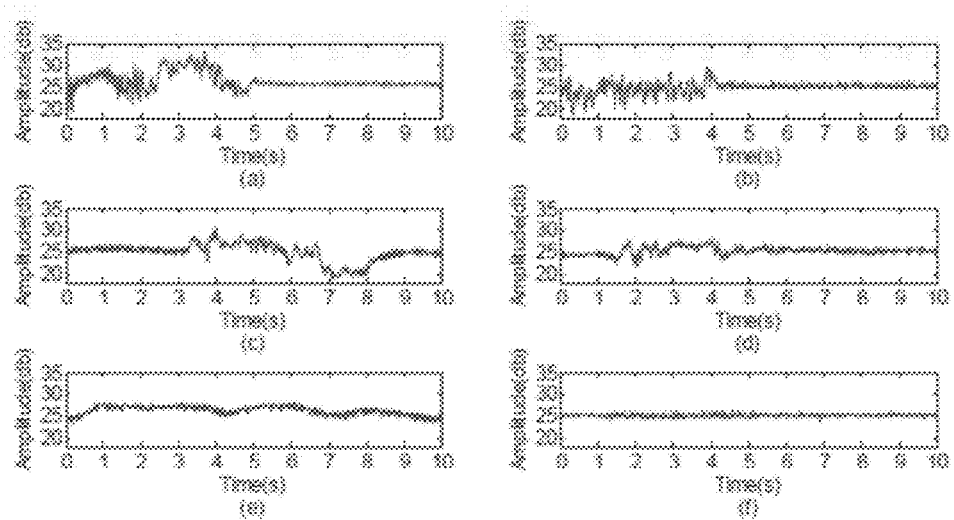
FIG. 3 shows activities vs. CSI amplitude in LOS and NLOS conditions: (a) LOS Walking-Fall, (b) NLOS Walking-Fall, (c) LOS Sit down, (d) NLOS Sit down, (e) LOS Standing, (f) NLOS Standing.

As daily activities can occur in different locations in the indoor environment, the inventors conduct activities in both LOS and NLOS conditions to see their impact. As illustrated in FIG. 3, the amplitude variance caused by human activities becomes weaker from LOS to NLOS conditions. This is expected because the signal propagation suffers from path loss. For example, as shown in red lines in FIG. 1, along with the motion of human body, the scattered paths from human body keep changing. With the distance between human body and LOS path increasing, those scattered power decreases rapidly until they become too weak to be distinguished from the environment noise. Then the inventors come up with the following questions: how far away will the CSI amplitude of the standing posture become indistinguishable from that of other immobile activities? And how far away will this base signal of motion activities become indistinguishable from that of immobile activities?

The inventors conduct extensive experiments in different rooms of different sizes, finding that the exact results vary slightly with respect to room settings and layouts. Using the settings the inventors adopt, the answer to the first question is around 2 m in multiple paths condition in a clear environment, and it drops to less than 1.5 m with a 1 m high wooden desk with an LCD desktop screen on it as an obstacle between the LOS and human. Considering the symmetry of both sides from LOS path, the inventors find that the coverage area is not enough for common rooms.

Hence, the inventors conclude that the ability of the CSI amplitude to distinguish the standing posture from other immobile activities is quite limited and unreliable in ordinary indoor living environments. The answer to the second question is 5 m without obstacles from LOS path and it is 4 m with the same wooden obstacle. Considering the symmetry of both sides from LOS path, the coverage area, even with 4 m, is big enough for a common living room. Hence, the ability of the CSI amplitude to distinguish the motion activities from immobile ones is enough and reliable in common living rooms.

Fall in Different Scenarios

Figure 4:
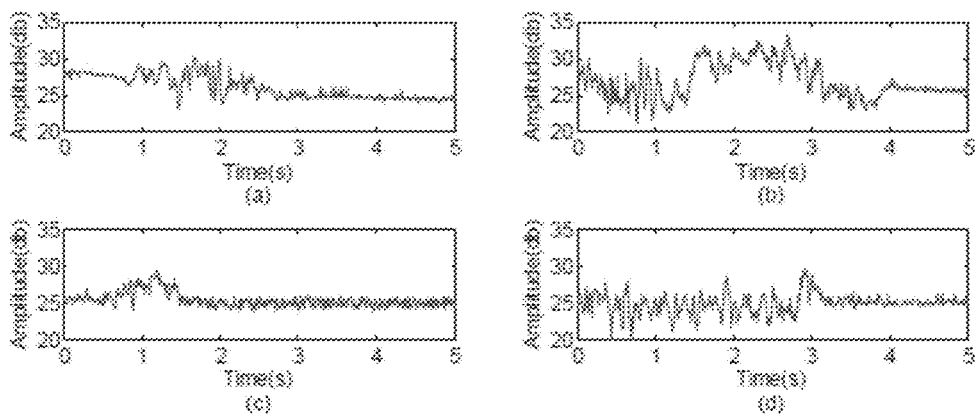
FIG. 4 shows fall in different scenarios: (a) Standing-Fall in LOS, (b) Walking-Fall in LOS, (c) Standing-Fall in NLOS, (d) Walking-Fall in NLOS.

The inventors focus on fall, i.e., standing-fall and walking-fall, occurred in different scenarios, including LOS and NLOS. As illustrated in FIG. 4, the amplitude variance shows a clear transition from a fluctuated state to a stable state among all activities. This is expected because fall often ends up with an immobile posture (e.g., lying on the floor/sofa) which results in a relatively stable signal change pattern. It seems that the inventors could use the transition as a feature for real-time activity segmentation. Unfortunately, as numerous human daily activities can end up with certain kind of immobile activities, singling out the real fall from all of these activity combinations is very difficult, or even impossible.

The prior art did make use of the above feature for real-time activity segmentation, for example, solution described in "Wifall: Device-free fall detection by wireless networks" by C. Han, K. Wu, Y. Wang and L. M. Ni, however, it oversimplifies the problem in two aspects, which limit its application range: First, the subject was assumed to stay in a controlled environment where only a few (four) predefined activities were performed. Hence when various undefined human activities are performed, the system will fail. Second, two predefined activities should be separated by an immobile activity in between. In other words, the subject cannot perform activities in a natural and continuous manner, e.g., one cannot stand up from the chair and walk, instead, he should stand up first, stand there for a while, and then walk. Hence, if the fall occurred during walking, WiFall cannot detect the fall because it fails to detect the starting reference point of the fall. The limitations of the CSI amplitude motivate the inventors to explore if a better base signal for activity segmentation and fall detection can be found.

Human Activities Vs. Phase of CSI

As human activities can cause channel distortion which also leads to signal phase shift, so the inventors follow the same logic of the last section to study the relationship between human activities and the phase information of CSI.

Phase Calibration

In one embodiment, the measured phase $\hat{\phi}_f$ of CSI of subcarrier f can be computed as follows:

$$\vec{\phi}_f = \phi_f + 2\pi f_\Delta \Delta t + \beta + Z_f$$

Where, $\phi_f$ is the true phase, $\Delta t$ is the time lag at the antenna, $\beta$ is an unknown constant phase offset, $Z_f$ is some measurement noise, $f_\Delta$ is the carrier frequency offset at the receiver.

The inventors find that the raw phases provided by commodity Intel 5300 NICs are randomly distributed and not usable, the reason lies in the term $2\pi f_\Delta \Delta t$; since $\Delta t$ is different across subsequent packets. Recent prior shows that on a single commodity wireless NIC, the RF oscillators are frequency locked at startup. So the $f_\Delta$ across different antennas on the same NIC is actually the same value. This inspires the inventors to compute the phase difference $\Delta \phi_f$ between two antennas as:

$$\Delta \hat{\phi}_f = \Delta \phi_f + 2\pi f_\Delta \varepsilon + \Delta \beta + \Delta Z_f$$

Where $\Delta \phi_f$ is the true phase difference, $\varepsilon = \Delta t1 - \Delta t2$ ($\Delta t1$ and $\Delta t2$ are time lags at the antenna 1 and 2 respectively). $\beta$ is the unknown constant phase difference offset, $\Delta Z_f$ is still the measurement noise. If the inventors put two receiver antennas at the distance around $\frac{1}{2}\lambda$ from each other, $\varepsilon$ indicates the propagation time of the distance differential $\Delta d$ (which is around $\frac{1}{2}\lambda \sin \theta$) between two antennas. Then $\varepsilon$ can be roughly estimated as follows:

$$e \approx \frac{1/2 \lambda \sin \theta}{cT} \leq \frac{1}{2Tf}$$

Where $\lambda$ is the wavelength, f is the central frequency, c is the speed of the light, T is the sample interval which is 50 ns in WiFi and $\theta$ is the direction of arrival. As the inventors select the WiFi setting running on 5 GHz frequency, $\varepsilon$ is thus approximately equal to zero. Thus, the inventors get the measured phase difference $\Delta \hat{\phi}_f$ as $$\Delta \hat{\phi}_f = \Delta \phi_f + \Delta \beta + \Delta Z_f$$

Phase Difference Across Different Subcarriers and Streams

The inventors have the similar observation for the phase difference as for the amplitude that human activities affect different subcarriers in a similar way and adjacent subcarriers behave similarly. From the CSI stream perspective, as the variances of the phase difference across two antennas is the sum of individual variance on each antenna, while implies that the phase difference is more sensitive to the environment changes than the amplitude, thus the CSI phase difference seems to be a better base signal compared to the CSI amplitude for characterizing human activities.

Figure 5:
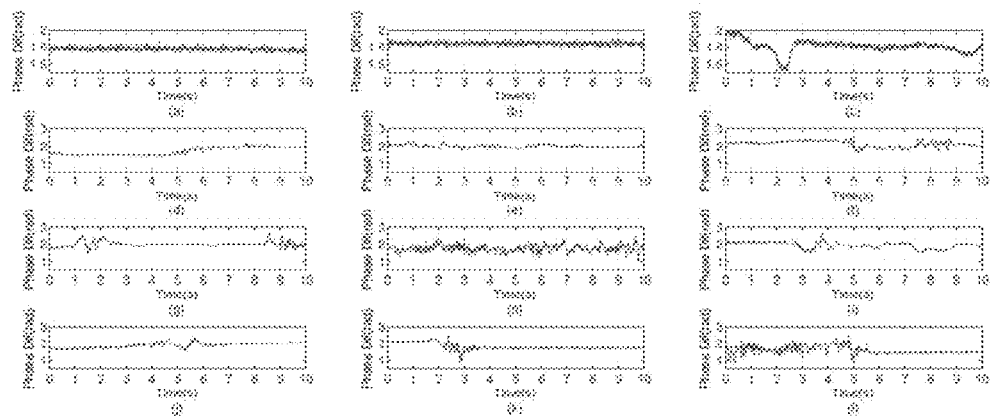
FIG. 5 shows phase difference of human motion activities: (a) Sitting, (b) Lying, (c) Standing, (d) Lie down, (e) Upper body activities, (f) Pickup, (g) Squat, (h) Walking, (i) Stand up, (j) Sit down, (k) Standing-Fall, (l) Walking-Fall.

Now the inventors observe the phase difference caused by immobile and motion activities, respectively. Impact of immobile human activities: As illustrated in FIG. 5(a-c), immobile activities such as sitting and lying, result in relatively stable signal patterns in time domain. One new observation is that the CSI phase difference signal fluctuates with the tiny human body movement. Specifically, the CSI phase difference during standing shows an obvious fluctuation compared to that caused by sitting and lying, and the inventors can see a clear difference between their patterns. As the inventors also note that the boundary blurs as a subject is standing far away from LOS path. Hence, the inventors cannot jump to a conclusion that the phase can reliably distinguish between the standing activity and other immobile activities. Impact of human motion activities: compared to immobile activities, motion activities lead to obvious CSI signal fluctuation in the time domain as illustrated in FIG. 5(d-l). Again, there is still no obvious pattern to differentiate the real fall from other non-fall daily activities.

Activities in LOS and NLOS Conditions

Figure 6:
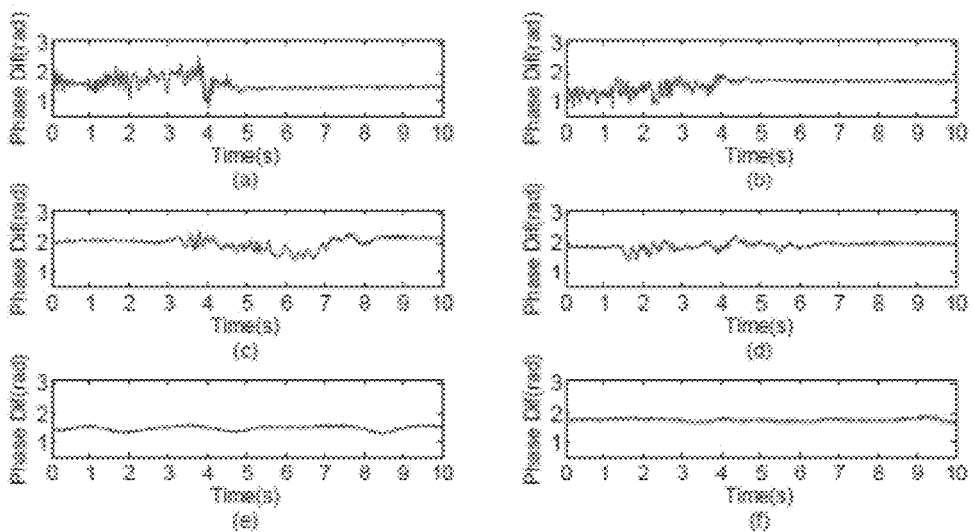
FIG. 6 shows activities vs. the phase difference in LOS and NLOS conditions: (a) LOS Walking-Fall, (b) NLOS Walking-Fall, (c) LOS Sit down, (d) NLOS Sit down, (e) LOS Standing, (f) NLOS Standing.

As illustrated in FIG. 6, it is not a surprise that the phase variance caused by human activities becomes weaker from LOS to NLOS conditions. Now the inventors answer the previous two questions with respect to phase difference.

With the setting the inventors adopt, the answer to the first question is around 3.5 m in a multiple paths clear environment and it drops to 3 m with a 1 m high wooden desk with an LCD desktop screen on it as an obstacle between the LOS and the human subject as the inventors did in 4.1.3. Compared to the amplitude, it seems that the CSI phase difference variance for the standing posture in both LOS and NLOS scenarios is amplified and the difference between the signal pattern of the standing and that of immobile activities becomes clearer. As the coverage area is enough for rooms with standard sizes, the inventors argue that the phase difference over two antennas proves to be a robust base signal to distinguish between lying (sitting) and standing. The answer to the second question is 6 m without obstacles from LOS path but it drops to 5 m with the same desk as an obstacle. Considering the symmetry of both sides from LOS path, the inventors conclude that the phase difference is also a better base signal than the amplitude to distinguish the motion activities from immobile ones in common living rooms.

Fall in Different Scenarios

Figure 7:
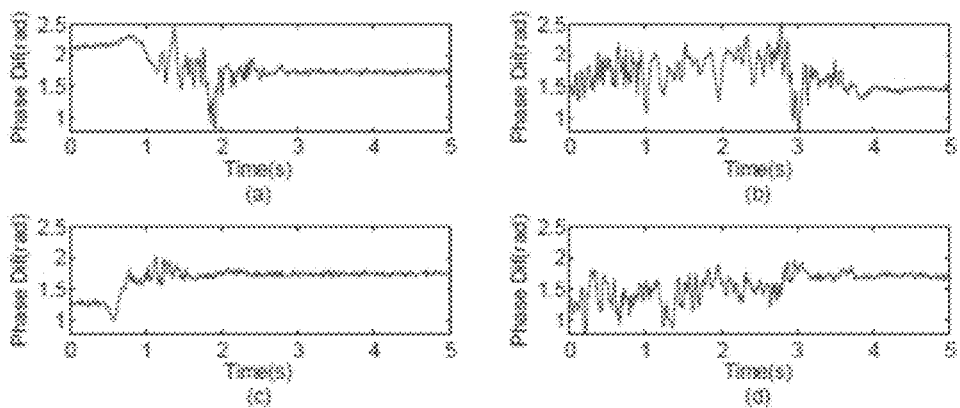
FIG. 7 shows fall in different scenarios: (a) Standing-Fall in LOS, (b) Walking-Fall in LOS, (c) Standing-Fall in NLOS, (d) Walking-Fall in NLOS.

As illustrated in FIG. 7, while most of the human activities, such as walking, running, standing and falling, all lead to obvious CSI phase difference fluctuation over time. Only several immobile activities, such as sitting still and lying, lead to very steady and stable signal pattern over the time. The inventors found that only when people fall, lie down and sit down, the variance of the phase difference exhibits an obvious transition from the fluctuation state to the stable one, and then the state transition of the CSI phase difference was used for real-time activity segmentation.

Through extensive experiments, the state transition of the CSI phase difference variance proves to be a robust feature in time domain to segment the fall activities from the continuously received CSI streams. However, many "in-place" activities besides falling down, lying down and sitting down might also cause the state transition of the CSI phase difference, which leads to a lot of activities segmented out. Here "in-place" means the subject is conducting particular limb motions while lying or sitting. The transition happens when the subject finishes certain in-place activities (such as eating, writing or making a phone call) and returns to the immobile postures. As there are different kinds of in-place activities, collecting all these activities for training and testing one by one for classification is a challenge.

Power Profile Versus Daily Activities

Figure 8:
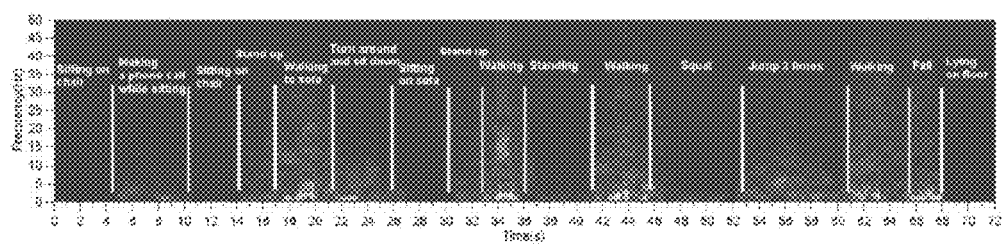
FIG. 8 shows spectrogram for a series of different activities.

In order to reveal more effective features for fall segmentation and detection, the inventors further use the Short-Time Fourier Transform to profile the spectrogram of the CSI phase difference signal corresponding to various daily activities. As shown in FIG. 8, it is interesting to see that different activities have different power profiles and the frequency range contributing to the power profile exhibits particular patterns. Specifically, the inventors notice that:

The immobile postures such as sitting still (0-4 s, 11-14 s, 27-30 s) and lying still (68-72 s) have a weak power profile, as there is no any obvious body movement.

The "in-place" activities such as making a phone call while sitting (4-10 s) and standing (36-41 s) have a mild power profile contributed mainly by the low frequency components (<5 Hz), which are generated mainly the limb movement.

All the motion activities such as walking (17-21 s, 33-36 s, 41-46 s, 61-65 s), standing up (14-17 s), jumping (53-61 s), turning around and sit down (21-26 s), and falling (66-68 s) have a strong power profile with both low frequency [0, 5 Hz] and high frequency components (>5 Hz), which are generated by both limb and torso movement.

While the falls and sitting/lying down activities show a sharp power profile decline from high frequency to low frequency components (68 s, 25 s), the "in-place" activities won't cause such a sudden power profile decline as the power profile of "in-place" activities mainly lies in the low frequency range (<5 Hz).

Hence, by detecting the state transition of the CSI phase difference variance along with the sharp power profile decline pattern, the inventors can robustly rule out the "in-place" activities but segment only the fall and a few other non-fall activities (i.e. lying down and sitting down). The inventors refer those few other non-fall activities as fall-like activities.

If the inventors focused on the power profile of the fall and fall-like activities, it is noticed that while the fall and fall-like activities both end up with a sharp power profile decline, the falls often exhibit even a sharper power profile decline pattern than the fall-like activities. For example, as shown in FIG. 8, comparing the power profile before and after the ending reference point of the fall (at 68 s), and that of the sit down activity (at 25 s), the inventors can see that the fall shows an gentle and slight power decline. This unique characteristic of fall is probably caused by the uncontrollable state of the subject, as when a person falls, he would lose control of the body and experiences an accelerated moving stage before hitting the floor. As the subject hits the floor, the moving speed of the body would change from high to zero, without a controlled de-accelerating stage like other fall-like activities such as sitting down.

However, the inventor also notice that this gap becomes unobvious as the speed of the fall-like activities increasing, i.e., the power profile decline pattern of some quick fall-like activities looks similar to that of the fall. In particular, when the speed of the fall-like activities increases to a comparable one with that of the falls, the inventors can no longer tell the difference only by comparing the power profile decline pattern.

Framework and Methodology

Figure 9:
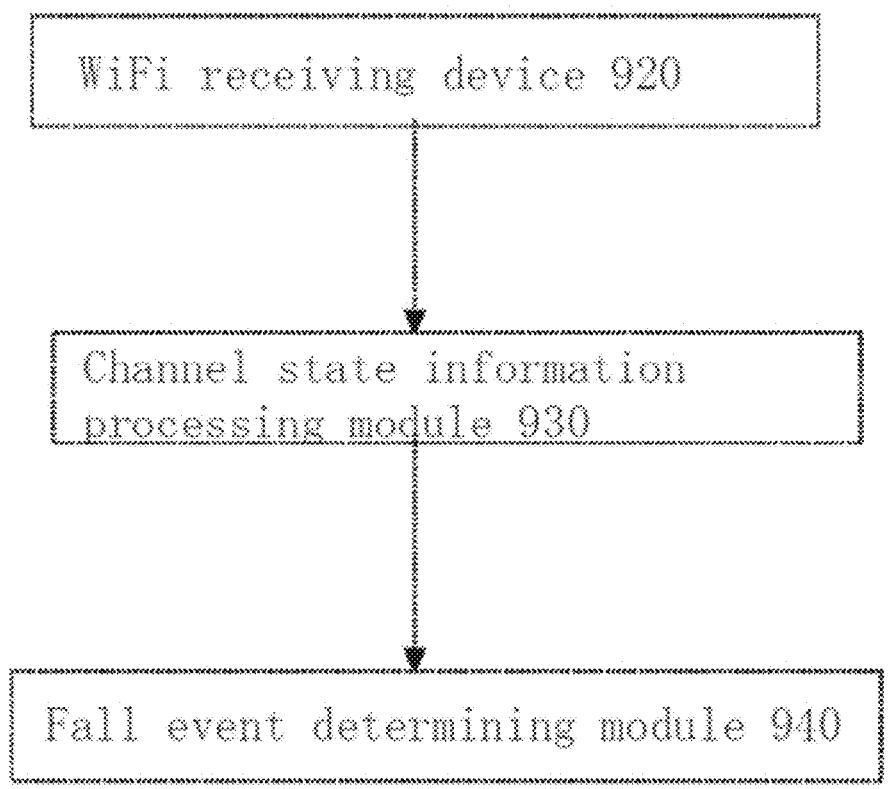
FIG. 9 shows a fall detection system framework according to an embodiment.
Figure 10:
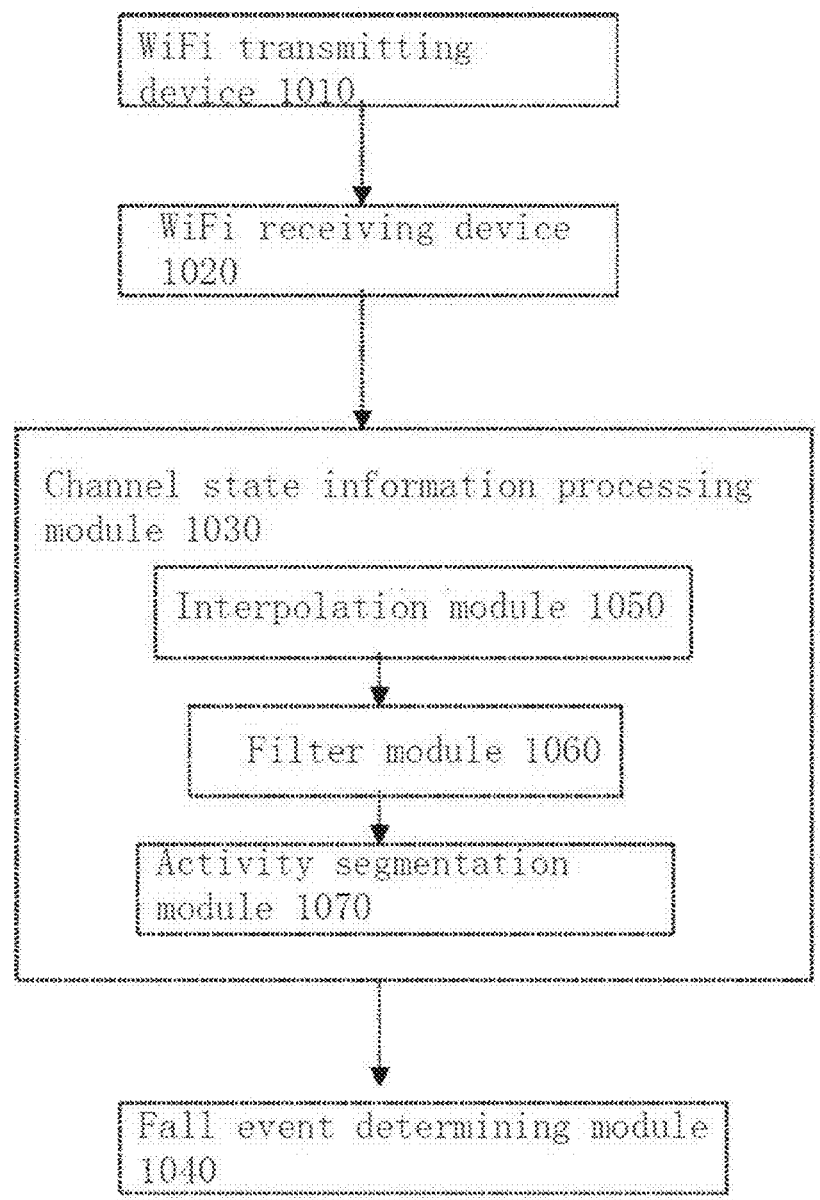
FIG. 10 shows a fall detection system framework according to another embodiment.

Now referring to FIGS. 9 and 10, which show the fall detection system of the present invention according to an illustrated embodiment. As illustrated in FIG. 9, the fall detection system comprises three functional modules: a WiFi receiving device 920, a channel state information processing module 930 and a fall event determining module 940. In one embodiment, the WiFi receiving device 920 can comprise a first receiving antenna and a second receiving antenna, wherein a first WiFi signal stream passing through an environment is received by the first receiving antenna, and a second WiFi signal stream passing through the environment is received by the second receiving antenna. In one embodiment, the Channel State Information processing module 930 can be configured to determine a physical layer Channel State Information stream, namely, a first CSI stream, of the first WiFi signal stream; determine a physical layer Channel State Information stream, namely, a second CSI stream, of the second WiFi signal stream; determine the phase difference, namely, CSI phase difference between the respective states of the physical layer Channel State Information stream of the first WiFi signal stream and the physical layer Channel State Information stream of the second WiFi signal stream at the same time point, to form a CSI phase difference stream. In an embodiment, the fall event determining module 940 can be configured to determine a fall event according to the CSI phase difference stream. In another embodiment, the fall event determining module 940 can be further configured to determine a fall event according to the CSI stream and CSI phase difference stream.

Further, as illustrated in FIG. 10, the fall detection system further comprises a WiFi transmitting device 1010, the channel state processing module of the fall detection system further comprises interpolation module 1050, filter module 1060 and activity segmentation module 1070. In one embodiment, the WiFi transmitting device uses orthogonal frequency division modulation (OFDM) in the physical layer. In one embodiment, the WiFi transmitting device 1010 transmits WiFi signal stream to environment by a transmitting antenna, wherein the first WiFi signal stream and the second WiFi signal stream are from WiFi signal transmitted by the transmitting antenna of the WiFi transmitting device 1010.

The fall detection system takes the CSI signal streams as input, which can be collected at the receiver side using two receiver antennas of a commodity WiFi device (e.g., Intel 5300 NIC). Each CSI signal stream contains CSI readings from 30 subcarriers on a wireless stream and totally two CSI streams are collected between one transmitter antenna and two receiver antennas. The CSI sampling rate is set to 100 pkts/s. The system can take advantage of CSI measurements from existing traffic across these links, or if insufficient network traffic is available, the system might also generate periodic traffic for measurement purposes.

Figure 11:
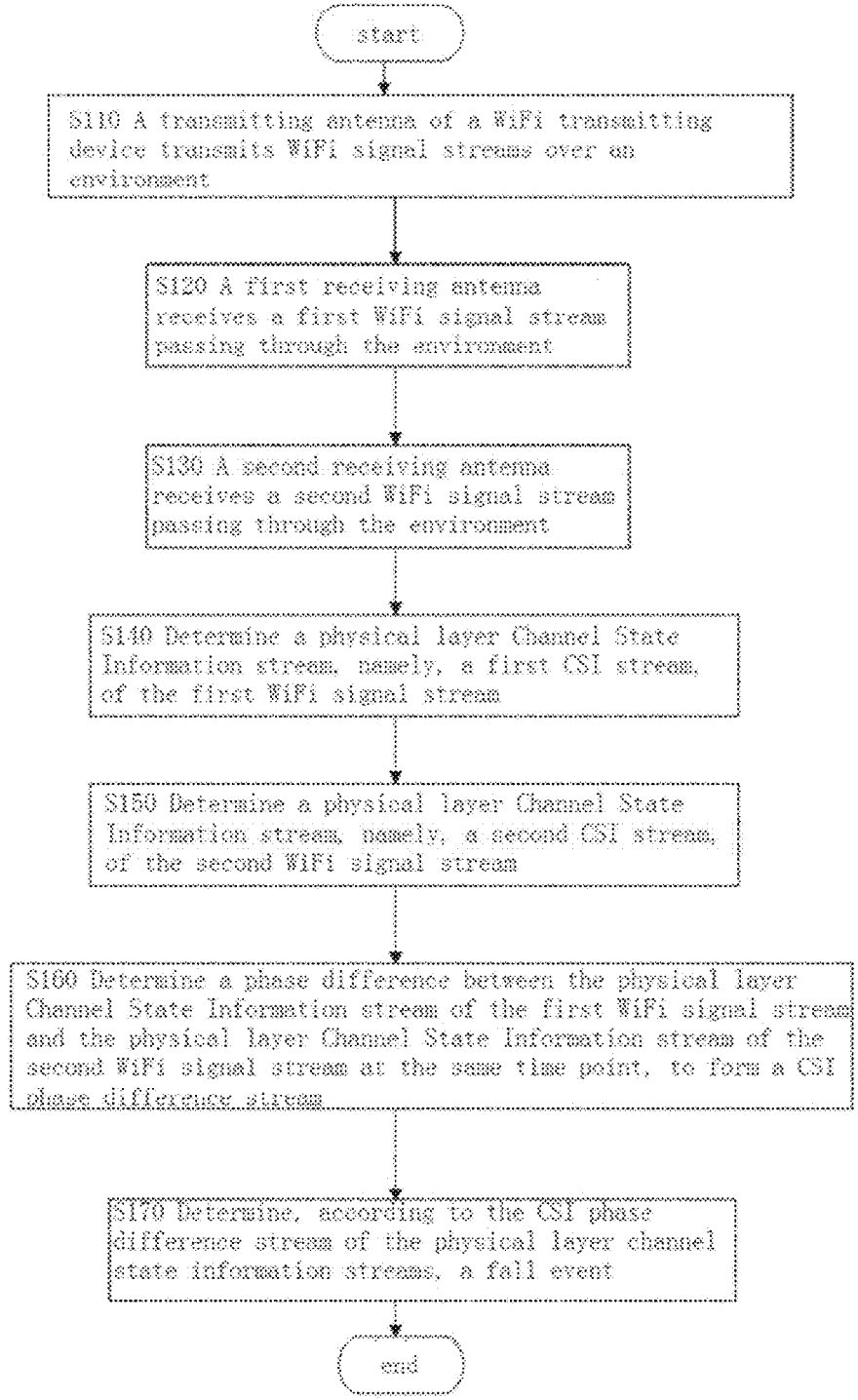
FIG. 11 shows a flow chart of a fall detection method according to an embodiment.

Now referring to FIG. 11, which shows a fall detection method of the present invention according to an illustrative embodiment. The process is performed by using the system illustrated in FIG. 10. The process begins with that WiFi signal streams are transmitted to the environment via a transmitting antenna of a WiFi transmitting device at S110. Wherein, in an embodiment, the WiFi transmitting device may use orthogonal frequency division modulation (OFDM) in the physical layer. This fall detection method, further comprising: receiving a first WiFi signal stream passing through the environment by a first receiving antenna at S120; receiving a second WiFi signal stream passing through the environment by a second receiving antenna at S130; determining a physical layer Channel State Information stream, namely, a first CSI stream, of the first WiFi signal stream at S140; determining a physical layer Channel State Information stream, namely, a second CSI stream, of the second WiFi signal stream at S150; determining a phase difference, namely, CSI phase difference, between the physical layer Channel State Information stream of the first WiFi signal stream and the physical layer Channel State Information stream of the second WiFi signal stream at the same time point, namely, a CSI phase difference, to form a physical layer Channel State Information difference stream, to form a CSI phase difference stream at S160; and determining a fall event according to the phase difference stream between the physical layer Channel State Information stream of the first WiFi signal stream and the physical layer Channel State Information stream of the second WiFi signal stream at the same time point, namely, the CSI phase difference stream at S170. In another embodiment, a fall event is determined according to the CSI stream and the phase different stream between physical layer Channel State Information stream of the first WiFi signal stream and the physical layer Channel State Information stream of the second WiFi signal stream, namely, determining a fall event according to the first CSI stream and the second CSI stream and the CSI phase difference stream.

Hereinafter, the fall detection system and method of the present invention are further described herein with reference to the accompanying drawings.

Channel State Information Processing:

The goal of signal processing is two-fold: 1) Dealing with the uneven arrival of signal packets caused by the bursty Wi-Fi transmissions; 2) Filtering out signal noises which won't contribute to fall segmentation and detection. In one embodiment, the Channel State Information processing module can be configured to determine the phase difference between the respective phase at the same time point in the interpolated first CSI stream and the interpolated second CSI stream, namely, the interpolated CSI phase difference, in order to form the interpolated CSI phase difference stream.

In another embodiment, the Channel State Information processing module can be configured to determine a physical layer Channel State Information stream, namely, a first CSI stream of the first WiFi signal stream; determine a physical layer Channel State Information stream, namely, a second CSI stream, of the second WiFi signal stream; and determine the phase difference, namely, CSI phase difference, between the respective phase of the physical layer Channel State Information stream of the first WiFi signal stream and the physical layer Channel State Information stream of the second WiFi signal stream at the same time point, to form a CSI phase difference stream. In one embodiment, the Channel State Information processing module further comprises interpolation module and filter module, which implement the above two goals by using interpolation and band-pass filter, respectively.

In one embodiment, the Channel State Information processing module can be further configured to: extract the following feature of the raw CSI phase difference stream and/or the filtered CSI phase difference stream: power decline ratio (PDR) (taking the determined finishing reference point of a fall and fall-like activities as a base time point, the power decline ratio (PDR) is determined as the energy decline ratio within a predetermined frequency range (for example, 0-50 Hz) within a predetermined time length before and after the base time point (for example, within two time windows of one second before and after) over the time-frequency spectrum).

Interpolation

Wi-Fi is a shared channel, where multiple devices use random access to share the medium. This results in the received packets that are not evenly spaced in time domain. Two problems may occur if the arrival of signal is not evenly spaced: the sampled CSI reading during a fall does not be continuous, which makes it difficult for feature extraction; 2) unevenly spaced samples in time domain prevent Time-Frequency analysis to get the spectrogram. In one embodiment, the interpolation module can be configured to interpolate in the first CSI stream in order to get the interpolated first CSI stream with continuous time-domain spectrogram; and interpolate in the second CSI stream in order to get the interpolated second CSI stream with continuous time-domain spectrogram. In one embodiment, the interpolation module uses the 1-D linear interpolation algorithm to process the raw CSI stream. Those skilled in the art can understand and use the 1-D linear interpolation algorithm to process the raw CSI stream according to the prior art. For example, for the use of the 1-D linear interpolation algorithm, see R. Nandakumar, B. Kellogg, and S. Gollakota, "Wi-fi gesture recognition on existing devices," arXiv preprint arXiv: 1411. 5394, 2014.

Band-Pass Filter

The interpolated CSI signal stream is then fed into a filter module, which can be configured to further rule out irrelevant signal frequency components from interpolated CSI phase difference stream in order to get the filtered CSI phase difference stream; in order to further rule out irrelevant signal frequency components. As the speed of chest movement caused by respiration or slight body movement are relatively low compared to that of the fall, the signal changes caused by these motions mainly lie in the lower frequency range, often within [0, 4 Hz]. Furthermore, these body motions are embedded in all the human activities. Hence, it is reasonable to conduct a band-pass filter to filter out the signal components which are below the frequency of 4 Hz. Through experiments, the frequency range that can filter-out the non-relevant activities yet well characterize the fall and fall-like activities lies in [5.10 Hz]. In one embodiment, filter module filters out the signal frequency components which are below 4 Hz. In another embodiment, filter module filters out the signal frequency components which are below 4 Hz and which are above 10 Hz.

Activity Segmentation

Activity segmentation module can be configured to identify the finishing reference point of fall and fall-like activities according to the CSI phase difference stream, and determine the starting reference point of fall and fall-like activities according to a trace back window size. It consists of two steps: in step one, the finishing reference point of the fall or fall-like activities is identified automatically by processing the variance of CSI phase difference; then in step two, the starting reference point of the fall or fall-like activities is determined by selecting a proper trace back window size from the finishing reference point.

In one embodiment, activity segmentation module can be further configured to: determine if a raw CSI phase difference signal and a filtered CSI phase difference signal are in a fluctuation state or a stable state by using a threshold-based sliding window method; and for the raw CSI phase difference signal and the filtered CSI phase difference signal, (such as according to their sliding standard deviation, respectively) detect the transition from the fluctuation state to the stable state, and determine a finishing reference point of fall and fall-like activities by checking if the two signals enter into the stable state and based on the time difference between the raw CSI phase difference signal and the filtered CSI phase difference signal when entering into the stable state, which is referred to as a time lag.

Identify the Finishing Point of Fall or Fall-Like Activities

In the empirical study section, it was found that the state transition of the CSI phase difference variance is a robust base signal to detect the fall and fall-like activities (e.g., lying down, sitting down). Based on the two observations described previously, the inventors propose a two-phase segmentation approach to separate the fall and fall-like activities from other activities in the continuously received CSI streams.

In phase one, the inventors use a threshold-based sliding window method to determine if the raw phase difference signal and the band-pass filtered phase difference signal are in the fluctuation state or stable state. This process consists of three steps: First, the inventors collect the two signal streams in stable state (e.g., lying/sitting in LOS path) across multiple sliding windows off-line and calculate their mean μ and the normalized standard deviation σ, respectively; Then, the inventors determine the threshold value for both signal streams as follows:

$$\mu+6\sigma \leq \delta$$

Figure 12:
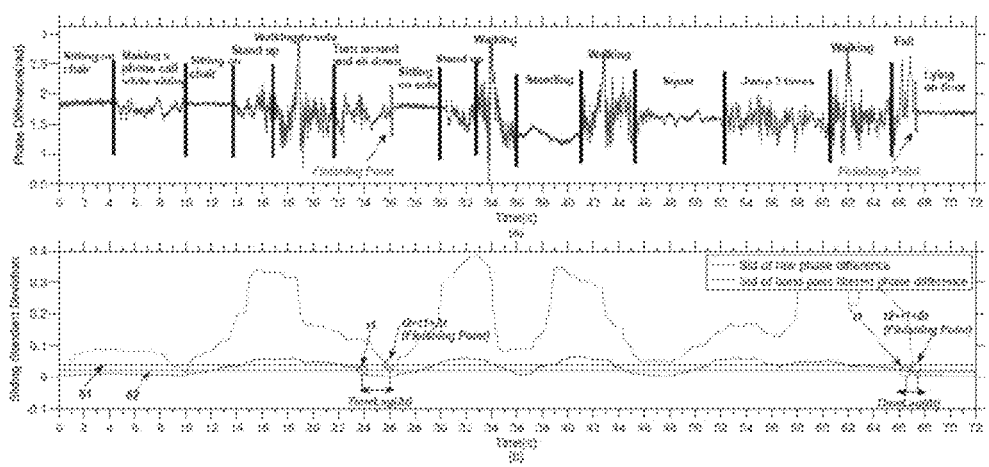
FIG. 12 shows fall and fall-like activities finishing point identification: (a) Phase difference across a continuously performed activities, (b) The sliding standard deviation of (a) $\delta 1$ and $\delta 2$ are the thresholds for the raw and band-pass filtered phase difference respectively.

In the last step of phase one, the inventors acquire the two signal streams in a sliding window on-line as shown in FIG. 12(b) and see if they are in the fluctuation state or stable state by comparing the mean value in the sliding window with the threshold. If the mean value is smaller than the threshold, the signal is said to be in the stable state, otherwise it is in the fluctuation state.

In phase two, the inventors detect the transition from the fluctuation state to stable state for both the raw phase difference signal and the band-pass filtered phase difference signal, and determine the finishing reference point of the fall and fall-like activities by checking if both signals enter the stable state. This process contains two steps: In step one, keep tracking of the state of two signals and checking if there is a transition occurring from the fluctuation state to stable state. When such a transition happens, the inventors mark the time t1 and start monitoring the state of the other signal. If the other signal also enters the stable state within a time lag Δt from t1, the inventors mark the time t2 as the finishing reference point of the fall and fall-like activities.

Wherein, in one embodiment, if and only if the raw CSI phase difference signal and the filtered CSI phase difference signal, (e.g., according to the respective sliding standard deviation and the corresponding predetermined threshold) enter the stable state with a time difference, namely, the time lag that is less than the predetermined threshold, determining a finishing reference point of fall and fall-like activities.

The rationale behind detecting the two signal state transitions for the fall and fall-like activities segmentation is: detecting the CSI phase difference transition as the first criteria, then filter out the "in-place" activities by checking the band-pass CSI phase difference variance. If only track the state transition of the raw phase difference variance, the "in-place" activities may also be segmented out as fall-like activities. As shown in the grey-dashed line of FIG. 12, when the subject stops making a phone call, the raw phase difference shows a state transition (at 9 s), which meets the inventors previous segmentation criteria. If only track the band-pass filtered CSI phase difference variance, the inventors will no longer distinguish the lying (sitting) from standing, as the energy-band caused by standing activity lies in the same frequency range as for the in-place activities. As shown in the solid-blue line of FIG. 12(b), when the subject finishes walking and then stands still, the band-pass filtered phase difference shows a transition (at 36 s) from the fluctuation state to stable state. As the fall is always accompanied by a CSI phase difference state transition and a sharp power profile decline where the energy from the high frequency to low frequency components all drops within a very short period of time, which inspires the inventors to track the state transitions of both signals as well as the time lag. In particular, the shorter the time interval is, the sharper the power profile decline is.

As shown in FIG. 12(a), the inventors depict the CSI phase difference of a series of activities performed continuously and label the corresponding activities. While FIG. 12(b) shows the fall and fall-like human activity finishing identification results based on segmentation approach of the inventors. It can be seen that only the fall and fall-like activities are identified, while other activities such as making a phone call, standing up and walking are left out.

Determine the Proper Trace Back Window Size for Fall Detection

Based on the CSI phase difference state transition detection, the inventors can identify the finishing reference point of fall and fall-like activities in the continuously captured WiFi signal streams.

To differentiate the fall from fall-like activities, the inventors need to decide the proper trace back window size to collect training data samples for accurate fall detection. Considering the duration and characteristics of the fall and other fall-like activities, the inventors choose a three-second window size, composing a two-second signal segment before the finishing reference point and a one-second signal segment after it, to represent the whole segmented activity stream. The rationale behind this choice is two-fold: (1) ensure the consistency of all falls; (2) maintain the uniqueness of the fall and fall-like activities. Although different falls may behave differently, when people lose control of their bodies till falling on to the ground, the last two seconds exhibit consistency among different falls because of the status of losing control. The reason why the inventors include the one second segment after the finishing reference point is that the inventors want to characterize the whole transition process of the fall which contains all the unique features of the fall and fall-like activities according to the inventors' previous observations.

Fall Detection

After determining the starting and finishing reference point of the fall and fall-like activities, only the CSI phase difference and amplitude of those activities are singled out. The goal of the fall event determining module is to separate the fall from fall-like activities. In one embodiment, the fall event determining module can be further configured to determine a fall event according to the raw CSI phase difference stream and/or the filtered CSI phase difference stream. In a further embodiment, the fall event determining module can be further configured to determine a fall event according to the time lag and the power decline ratio (PDR) of the raw CSI phase difference stream and/or the filtered CSI phase difference stream by using one-class Support Vector Machine (SVM).

Feature Extraction

In one embodiment, Channel State Information processing module can be further configured to extract the following features of the first CSI stream or the second CSI stream: the normalized standard deviation (STD), the median absolute deviation (MAD), the offset of signal strength, interquartile range (IR), signal entropy, and the velocity of signal change; extract the following features of the raw CSI phase difference stream and/or the filtered CSI phase difference stream: the normalized standard deviation (STD), the median absolute deviation (MAD), the offset of signal strength, interquartile range (IR), signal entropy, and the velocity of signal change; and determine a fall event by using one-class Support Vector Machine (SVM) according to the features extracted by the feature extraction device.

Through extensive study, the inventors extracted the following eight features from the real time captured CSI streams for activity classification: (1) the normalized standard deviation (STD), (2) the median absolute deviation (MAD), (3) the offset of signal strength, (4) interquartile range (IR), (5) signal entropy, (6) the velocity of signal change, (7) the time lag, (8) the power decline ratio (PDR). In the prior art, those skilled in the art can understand and use the first six features. For example, for use and explain of the first six features, reference may be made to "Wifall: Device-free fall detection by wireless networks" by C. Han, K. Wu, Y. Wang and L. M. Ni (NFOCOM, 2014 Proceedings IEEE.IEEE, 2014, pp. 271-279). Therefore, only the two new features (7) the time lag, (8) the power decline ratio (PDR) are elaborated in the description.

Both Time Lag and PDR are proposed based on the observation that the fall and fall-like activities are different from the signal power spectrogram perspective. The time lag characterizes the time delay of the state transition point between the band-pass filtered and the raw phase difference as shown in FIG. 12(b), the inventors can see that the time lag for the fall is usually much shorter than that of the sit down activity. If the inventors compute the one-second accumulated power before and after the finishing point, then the PDR is defined as the power decline ratio which is the one-second power loss divided by the one-second accumulated power before the finishing point. PDR is computed with the following mathematical formula:

$$TD-FD = \frac{\sum_{t=\hat{t}_1}^{\hat{t}} \sum_{f=f_l}^{f_h} e_{t,f} \omega_f - \sum_{t=\hat{t}}^{\hat{t}+1} \sum_{f=f_l}^{f_h} e_{t,f} \omega_f}{\sum_{t=\hat{t}_{-1}}^{\hat{t}} \sum_{f=f_l}^{f_h} e_{t,f} \omega_f}$$

Where $\hat{t}$ is the finishing reference point, $\hat{t}-1$ is the instant of one second before $\hat{t}$ and the $\hat{t}+1$ is that of one second after $\hat{t}$. $f_l$ and $f_h$ refer to the frequency range from [0, 50 Hz]. $e_{t,f}$ is the power strength of a specific frequency f at a specific time t. $\omega_f$ is the weight vector for each frequency f.

Different from the prior art that only extracts features from the CSI amplitude information, the inventors extract the first six features from both CSI amplitude and phase difference, and extract the two new features from phase difference only. They together constitute the input of the SVM Classifier.

SVM Classifier

To detect the fall among the segmented activities, a one-class Support Vector Machine (SVM) is applied using the features extracted above. In the prior art, those skilled in the art can understand and use one-class Support Vector Machine (SVM). For example, for the use of one-class Support Vector Machine (SVM), see B. Scholkopf, J. C. Platt, J. Shawe-Taylor, A. J. Smola and R. C. Williamson, "Estimating the support of a high-dimensional distribution," Neural computation, vol. 13, no. 7, pp. 1443-1471, 2001. In one-class SVM, all the samples are divided into subjective class (i.e., the fall) and non-subjective class (i.e., fall-like activities). To solve the non-linear classification problem, it maps input samples into a high dimensional feature space by using a kernel function and finds the maximum margin hyperplane in the transformed feature space. SVM classifier requires a training data set and test data set. In the process of classification model construction, fall and fall-like activities are segmented and labeled in the continuously captured WiFi wireless signal streams in the activity segmentation phase. Then the extracted features along with the corresponding labels are fed into the SVM classifier to build the classification model. In the process of real-time fall detection, the classification results along with the data samples will be recorded. Using the user feedback, the wrong classification results will be re-labeled correctly and the model updating process will be triggered in time to update the classification model. Build the classification model by utilizing LibSVM.

Evaluation

In this section, the inventors present the implementation and evaluation results of RT-Fall system using commercial off-the-shelf WiFi devices.

Experimental Setups

The inventors evaluate our RT-Fall system using an 802.11n WiFi network with one off-the-shelf WiFi device (e.g., a dell laptop with two internal antennas) and one commercial wireless access point (e.g., TP-Link WDR5300 Router with one antenna running on 5 GHz). The laptop is equipped with an Intel WiFi Link 5300 card for measuring CSI. The signal transmission rate is set to 100 pkts/s.

Figure 13:
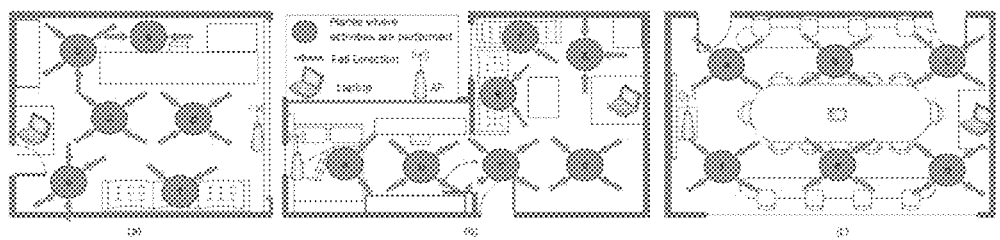
FIG. 13 shows three test rooms: Office (a), Apartment (b), Meeting Room (c).

The inventors conduct experiments in three rooms of different sizes to test the generality of the inventors system. The settings in these three places are shown in FIG. 13. The first place (e.g., office) has the size of about 3 m*4 m with one sofa, two tables and one bookcase, the second place (e.g., apartment with one bedroom and one living room) is about 6 m*2.5 m with a group of sofas, two tables and one bed, the third place (e.g. meeting room) is about 6 m*6 m with numerous tables and chairs around.

Data Set

Figure 14:
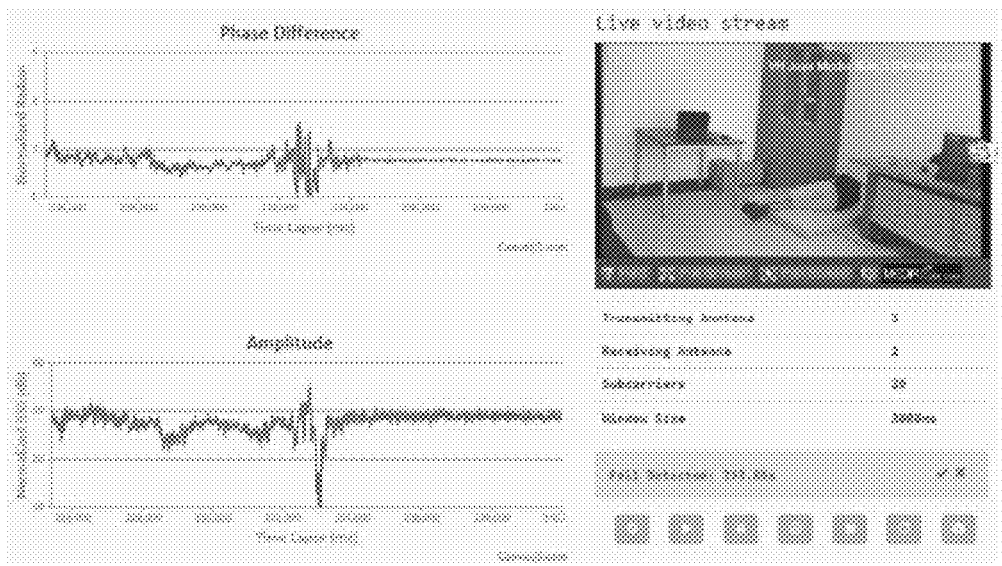
FIG. 14 shows user interface.

The inventors recruit one female and five male students to perform various daily activities in the three test rooms over two months. Each data record consists of a few continuous activities, mixing the fall, fall-like and other daily activities. The inventors mount a camera in each room to record the activities conducted as the ground truth. Over the test days, the chairs were moved to different places and the items on tables, such as bottles and bags, were moved, as usually occurred in daily life. During the experiments, the door of the room kept closed, and there was no other furniture movement. The web-based user interface of the inventors' system is shown in FIG. 14, where the recorded video, the amplitude and phase difference of CSI, the segmented activity CSI stream, and the detection results are updated on-line in real-time. When the system is started, a subject can perform any activities naturally and continuously, and the system will automatically segment CSI streams and report the segmentation/detection results in real-time on the user interface. It is very easy for the user to label the segmented activities with the user interface according to the evaluation results and the ground truth of the RT-FALL system.

Baseline Method and Performance Metrics

In the experiments, the inventors use the state-of-art fall detector proposed in "Wifall: Device-free fall detection by wireless networks" by C. Han, K. Wu, Y. Wang and L. M. Ni (NFOCOM, 2014 Proceedings IEEE.IEEE, 2014, pp. 271-279) as the baseline. Since WiFall cannot segment the fall and other daily activities reliably, the inventors thus leverage the inventors proposed method to segment the fall and fall-like activities, subsequently the inventors compare its activity classification performance with that of our approach using the inventors' data set. The inventors use the following two standard metrics for performance evaluation—sensitivity and specificity. Confusion matrix showed in Table 1 is used to define sensitivity and specificity.

TABLE 1

|  | Classified as Fall | Classsified as not Fall |
| --- | --- | --- |
| Is Fall | TP (True Positive) | FN (False Negative) |
| Is not Fall | FP (False Positive) | TN (True Negative) |

Sensitivity is defined as the percentage of correctly detected falls:

a. sensitivity=$TP/(TP+FN)$

Specificity is defined as the percentage of correctly detected non-fall activities:

specificity=$TN/(TN+FP)$

System Performance Vs. Number of Participants

The inventors notice different people perform activities in different ways. For example, some sit down faster, while some fall slower. Therefore, the inventors design a set of experiments in the office room to study the system performance with respect to the number of participants involved. Considering that the activities can occur in different places and from different directions as shown in FIG. 13(a), the inventors ask the participants to evenly cover all the situations when they perform experiments.

Figure 15:
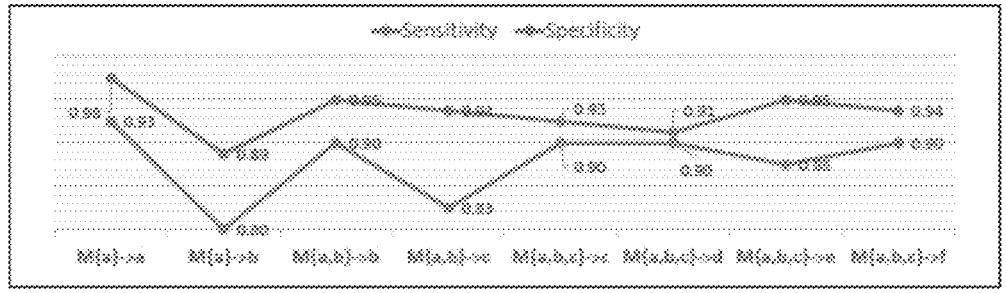
FIG. 15 shows system performance vs. number of participants: (a) Experiment design; (b) Performance evaluation with different number of people, M{S}->x means building the model M{S} from the training data of the people set S to evaluate the performance with the dataset of user x.

As shown in FIG. 15(a), the experiments consist of two phases: training data collection phase and testing phase. In the training data collection phase, each subject conducts 100 falls and fall-like activities respectively, and the system uses the training data from the people set S to build the model M {S}. In the testing phase, each subject x conducts 40 falls and 80 fall-like activities respectively to evaluate the performance using the model built from the training data of the people set S, and the evaluation results of each experiment group are shown in FIG. 15(b), where the classification model M is built with the training data set and the tests are done using those models for different number of participants. For example, at the beginning, as the training data set is empty, the inventors collect training data from the first subject a to build a model M {a} (see first row in FIG. 15(a)), which refers to the model built with one participant's data set (user a), and then test the performance on subject a using model M {a} from the training data of itself (see second row M {a}→a). Then the second subject participants in the experiments to evaluate the performance using the model M {a} (see third row M {a}→b) to see if the inventors can get consistent performance as the first subject. If not, the inventors can go on collect training data set from the second subject (see fourth row) to increase the training data set and build the model M {a, b}, and so on so forth, until the inventors get roughly consistent performance with the smaller training data set.

According to FIG. 15(b), M {a}→a has the best result, but it lacks generality to detect falls of other people accurately; with the number of participants increasing to three, the performance trends to converge, which is a little lower than that of M {a}→a. This is expected because M {a}→a corresponds to a personalized model, whereas M {a, b, c} corresponds to a generalized one that is trained for more people. Furthermore, according to the videos recorded, in the training and testing phases, all the 620 falls are 100% segmented out. Averaging the performance of the last three experiment groups, i.e., M {a, b, c}→d, e, f, the inventors achieve 93% of sensitivity and 89% of specificity in the office room.

Performance Comparison

Figure 16:
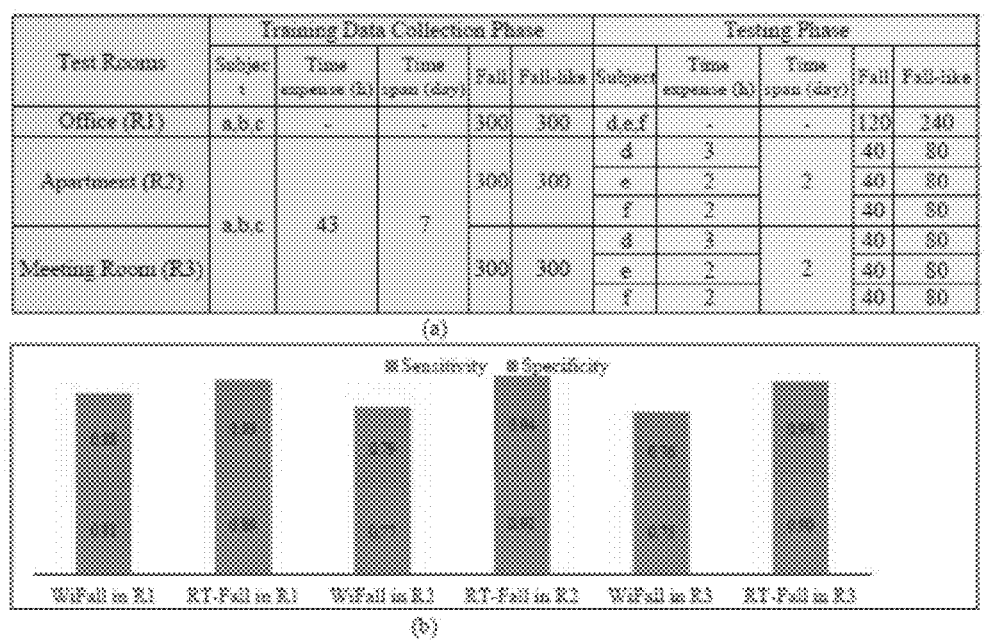
FIG. 16 shows performance comparison in different rooms: (a) Experiment Design; (b) Performance Results.

The inventors design experiments in three places as shown in FIG. 16(a) to compare the performance of RT-Fall with that of the baseline method WiFall. As the inventors have already collected training and testing data in preceding section in the office room, the inventors spent one more week in an apartment and meeting room with the three students (a, b, c) in the training data collection phase. Two classification models were built for each room, one is based on the inventors' approach, and the other is based on WiFall. In the testing phase, three new students (d, e, f) are invited to evaluate the performance of both models using the training data set of the people set (a, b, c). Averaging the evaluation results by the three new students for each room, the inventors get the performance comparison results in FIG. 16(b). In general, RT-Fall achieves 90% of sensitivity and 92% of specificity. Compared to the baseline method WiFall, RT-Fall gets 13% higher sensitivity and 11% higher specificity.

In the flowcharts and block diagrams described in different embodiments, shows that some possible structures, functionalities and operations of the device and method in different embodiments. In an alternative embodiment, one or more of the steps described in the flowchart may not be performed in the order shown in the drawings. For example, in some cases, the steps in the two blocks shown in succession may be performed substantially concurrently, or may sometimes be performed in the reverse order, depending on the function involved. Furthermore, in addition to the boxes shown in the flowchart and block diagrams, other blocks may be added.

For the purpose of illustration and description, the invention gives a description of various different embodiments, the description is not intended to be exhaustive or to limit the embodiments to the disclosed form. To those skilled in the art, there are many obvious changes within the protected scope of the claims. Different embodiments may provide different advantages. The purpose of selecting the described embodiments is to better explain the principles of the embodiments, their practical application, and enable those skilled in the art to understand the embodiments of the present invention with various modifications, which are conceived and adapted to specific applications.

The present invention further comprises the following clauses:

Clause 1. A fall detection method, comprising:

receiving, by a first receiving antenna, a first WiFi signal stream passing through an environment;

receiving, by a second receiving antenna, a second WiFi signal stream passing through the environment;

determining a physical layer Channel State Information stream, namely, a first CSI stream, of the first WiFi signal stream;

determining a physical layer Channel State Information stream, namely, a second CSI stream, of the second WiFi signal stream;

determining a phase difference, namely, a CSI phase difference, between respective phase of the physical layer Channel State Information stream of the first WiFi signal stream and the physical layer Channel State Information stream of the second WiFi signal stream at the same time point, to form a CSI phase difference stream; and determining, according to the CSI stream and the CSI phase difference stream, a fall event.

Clause 2. The fall detection method according to Clause 1, further configured to determine a fall event according to the first and the second CSI stream.

Clause 3. The fall detection method according to Clause 1, wherein further comprising transmitting the WiFi signal stream to the environment by a transmitting antenna of a WiFi transmitting device, wherein the first WiFi signal stream and the second WiFi signal stream are from WiFi signal transmitted by the transmitting antenna of the WiFi transmitting device.

Clause 4. The fall detection method according to Clause 3, wherein the WiFi transmitting device uses orthogonal frequency division modulation, i.e., OFDM, in the physical layer.

Clause 5. The fall detection method according to Clause 1, wherein further comprising: identifying the finishing reference point of fall and fall-like activities according to the CSI phase difference stream, and determining the starting reference point of fall and fall-like activities according to the trace back window size.

Clause 6. The fall detection method according to Clause 5, wherein further comprising:

interpolating in the first CSI stream to obtain an interpolated first CSI stream with a continuous time-frequency domain spectrum;

interpolating in the second CSI stream to obtain an interpolated second CSI stream with a continuous time-frequency domain spectrum; determining a phase difference, namely, a interpolated CSI phase difference, between respective phase of the interpolated first CSI stream and the interpolated second CSI stream at the same time point, to form a interpolated CSI phase difference stream;

removing the uncorrelated signal frequency components from the interpolated CSI phase difference stream to obtain a filtered CSI phase difference stream;

wherein, identifying the finishing reference point of fall or fall-like activities according to the filtered CSI phase difference stream, and determining the starting reference point of fall or fall-like activities according to the trace back window size.

Clause 7. The fall detection method according to Clause 6, wherein removing the uncorrelated signal frequency components according to a predetermined threshold.

Clause 8. The fall detection method according to Clause 6, wherein determining if a raw CSI phase difference signal and a filtered CSI phase difference signal are in a fluctuation state or a stable state by using a threshold-based sliding window method; and for the raw CSI phase difference signal and the filtered CSI phase difference signal, detecting the transition from the fluctuation state to the stable state, and determining a finishing reference point of fall and fall-like activities by checking if the two signals enter into the stable state and based on the time difference between the raw CSI phase difference signal and the filtered CSI phase difference signal when entering into the stable state, which is referred to as a time lag.

Clause 9. The fall detection method according to Clause 8, wherein further comprising:

wherein if and only if the raw CSI phase difference signal and the filtered CSI phase difference signal enter the stable state with a time difference, namely, the time lag, that is less than the predetermined threshold, determining a finishing reference point of fall and fall-like activities.

Clause 10. The fall detection method according to Clause 9, wherein the predetermined threshold is 2 s.

Clause 11. The fall detection method according to Clause 8 or 9, wherein further comprising:

extracting the following feature of the raw CSI phase difference stream and/or the filtered CSI phase difference stream: power decline ratio (PDR), which is determined to be the energy decline ratio within a predetermined frequency range before and after a predetermined time length of a base time point over the time-frequency spectrum, respectively, wherein the finishing reference point of fall and fall-like activities is determined as the base time point; and determining a fall event according to the raw and/or the filtered CSI phase difference streams.

Clause 12. The fall detection method according to Clause 9, wherein determining a fall event by using one-class Support Vector Machine (SVM) according to the time lag and the power decline ration of the raw CSI phase difference stream or filtered CSI phase difference stream.

Clause 13. The fall detection method according to Clause 12, wherein further comprising:

extracting the following features of the first CSI stream or the second CSI stream: the normalized standard deviation (STD), the median absolute deviation (MAD), the offset of signal strength, interquartile range (IR), signal entropy, and the velocity of signal change;

extracting the following features of the raw CSI phase difference stream and/or the filtered CSI phase difference stream: the normalized standard deviation (STD), the median absolute deviation (MAD), the offset of signal strength, interquartile range (IR), signal entropy, and the velocity of signal change; and determining a fall event by using one-class Support Vector Machine (SVM) according to the features extracted by the feature extraction device.

Clause 14. A fall detection system, comprising:

a WiFi receiving device comprising a first receiving antenna and a second receiving antenna, wherein a first WiFi signal stream passing through an environment is received by the first receiving antenna, and a second WiFi signal stream passing through the environment is received by the second receiving antenna;

a Channel State Information (CSI) processing module configured to: determine a physical layer Channel State Information (CSI) stream, namely, a first CSI stream of the first WiFi signal stream; determine a physical layer Channel State Information (CSI) stream, namely, a second CSI stream, of the second WiFi signal stream; and determine the phase difference, namely, CSI phase difference, between the respective states of the physical layer Channel State Information (CSI) stream of the first WiFi signal stream and the physical layer Channel State Information (CSI) stream of the second WiFi signal stream at the same time point, to form a CSI phase difference stream;

a fall event determining module configured to determine a fall event according to the CSI phase difference stream.

Clause 15. The fall detection system according to Clause 14, the fall event determining module is further configured to determine a fall event according to the CSI stream.

Clause 16. The fall detection system according to Clause 14, wherein further comprising a WiFi transmitting device which transmits the WiFi signal stream to the environment by a transmitting antenna of a WiFi transmitting device, wherein the first WiFi signal stream and the second WiFi signal stream are from WiFi signal transmitted by the transmitting antenna of the WiFi transmitting device.

Clause 17. The fall detection system according to Clause 14, wherein the WiFi transmitting device uses orthogonal frequency division modulation, i.e., OFDM, in the physical layer.

Clause 18. The fall detection system according to Clause 14, wherein the Channel State Information processing module further comprising:

an activity segmentation module configured to identify the finishing reference point of fall or fall-like activities according to the CSI phase difference stream, and determine the starting reference point of fall or fall-like activities according to a trace back window size.

Clause 19. The fall detection system according to Clause 18, wherein the Channel State Information processing module further comprising a interpolation module and filter module, wherein:

the interpolation module is configured to interpolate in the first CSI stream to obtain an interpolated first CSI stream with a continuous time-frequency domain spectrum; and interpolate in the second CSI stream to obtain an interpolated second CSI stream with a continuous time-frequency domain spectrum;

the Channel State Information processing module is further configured to determine a phase difference, namely, a interpolated CSI phase difference, between respective phase of the interpolated first CSI stream and the interpolated second CSI stream at the same time point, to form a interpolated CSI phase difference stream;

the filter module is configured to remove the uncorrelated signal frequency components from the interpolated CSI phase difference stream to obtain a filtered CSI phase difference stream;

the activity segmentation module is further configured to identify the finishing reference point of fall or fall-like activities according to the filtered CSI phase difference stream, and determine the starting reference point of fall or fall-like activities according to the trace back window size.

Clause 20. The fall detection system according to Clause 19, wherein the filter module removes the uncorrelated signal frequency components according to a predetermined threshold.

Clause 21. The fall detection system according to Clause 19, wherein the activity segmentation module is further configured to:

determine if a raw CSI phase difference signal and a filtered CSI phase difference signal are in a fluctuation state or a stable state by using a threshold-based sliding window method;

and for the raw CSI phase difference signal and the filtered CSI phase difference signal, detecting the transition from the fluctuation state to the stable state, and determining a finishing reference point of fall and fall-like activities by checking if the two signals enter into the stable state and based on the time difference between the raw CSI phase difference signal and the filtered CSI phase difference signal when entering into the stable state, which is referred to as a time lag.

Clause 22. The fall detection system according to Clause 21, wherein:

if and only if the raw CSI phase difference signal and the filtered CSI phase difference signal enter the stable state with a time difference, namely, the time lag, that is less than the predetermined threshold, determining a finishing reference point of fall and fall-like activities.

Clause 23. The fall detection system according to Clause 22, wherein the predetermined threshold is 2 s.

Clause 24. The fall detection system according to Clause 21 or 22, wherein, the Channel State Information processing module is further configured to: extracting the following feature of the raw CSI phase difference stream and/or the filtered CSI phase difference stream: power decline ratio (PDR), which is determined to be the energy decline ratio within a predetermined frequency range before and after a predetermined time length of a base time point over the time-frequency spectrum, respectively, wherein the base time point is the determined finishing reference point of fall and fall-like activities; and the fall event determining module is further configured to determine a fall event according to the raw and/or the filtered CSI phase difference streams.

Clause 25. The fall detection system according to Clause 21, wherein the fall event determining module is further configured to determine a fall event by using one-class Support Vector Machine (SVM) according to the time lag and the power decline ration of the raw CSI phase difference stream and/or filtered CSI phase difference stream.

Clause 26. The fall detection system according to Clause 25, wherein the Channel State Information processing module is further configured to extract the following features of the first CSI stream or the second CSI stream: the normalized standard deviation (STD), the median absolute deviation (MAD), the offset of signal strength, interquartile range (IR), signal entropy, and the velocity of signal change;

extract the following features of the raw CSI phase difference stream and/or the filtered CSI phase difference stream: the normalized standard deviation (STD), the median absolute deviation (MAD), the offset of signal strength, interquartile range (IR), signal entropy, and the velocity of signal change; and determine a fall event by using one-class Support Vector Machine (SVM) according to the features extracted by the feature extraction device.

What is claimed is:

1. A fall detection method, comprising:
receiving, by a first receiving antenna, a first WiFi signal stream propagating through an environment;
receiving, by a second receiving antenna, a second WiFi signal stream propagating through the environment;
determining a physical layer Channel State Information (CSI) stream, namely, a first CSI stream, of the first WiFi signal stream;
determining a physical layer Channel State Information stream, namely, a second CSI stream, of the second WiFi signal stream;
determining a phase difference, namely, a CSI phase difference, between a respective phase of the first CSI stream of the first WiFi signal stream and the second CSI stream of the second WiFi signal stream at the same time point, to form a CSI phase difference stream; and
determining, according to the CSI phase difference stream, a fall event.

2. The fall detection method according to claim 1, further comprising determining, according to the first and second CSI streams and the CSI phase difference stream, the fall event.

3. The fall detection method according to claim 2, further comprising determining if a raw CSI phase difference signal and a filtered CSI phase difference signal are in a fluctuation state or a stable state by using a threshold-based sliding window method; and for the raw CSI phase difference signal and the filtered CSI phase difference signal, detecting the transition from the fluctuation state to the stable state, and determining a finishing reference point of fall and fall-like activities by checking if the two signals enter the stable state and based on a time difference between the raw CSI phase difference signal and the filtered CSI phase difference signal when entering the stable state.

4. The fall detection method according to claim 3, further comprising:
extracting the following feature of the raw CSI phase difference stream and/or the filtered CSI phase difference stream: power decline ratio (PDR), which is determined to be the energy decline ratio within a predetermined frequency range before and after a predetermined time length of a base time point over a time-frequency spectrum, respectively, wherein the base time point is the determined finishing reference point of fall and fall-like activities; and
determining, according to the raw CSI phase difference stream and/or the filtered CSI phase difference stream, the fall event.

5. The fall detection method according to claim 4, wherein further comprising:
extracting the following features of the first CSI stream or the second CSI stream:
a normalized standard deviation (STD), a median absolute deviation (MAD, an offset of signal strength, interquartile range (IR), signal entropy, and a velocity of signal change;
extracting the following features of the raw CSI phase difference stream and/or the filtered CSI phase difference stream: the normalized standard deviation (STD), the median absolute deviation (MAD), the offset of signal strength, interquartile range (IR), signal entropy, and the velocity of signal change; and
determining, according to the features extracted by a feature extraction device, by using a one-class Support Vector Machine (SVM), the fall event.

6. The fall detection method according to claim 1, further comprising:
identifying a finishing reference point of fall and fall-like activities according to the CSI phase difference stream, and determining a starting reference point of fall and fall-like activities according to a trace back window size.

7. The fall detection method according to claim 3, wherein if and only if the raw CSI phase difference signal and the filtered CSI phase difference signal enter the stable state with the time difference, namely, a time lag, that is less than a predetermined threshold, determining the finishing reference point of fall and fall-like activities.

* * * * *